United States Patent [19]

Holzmann

[11] 4,191,748

[45] Mar. 4, 1980

[54] NOVEL MEDICINAL COMPOSITION, ESPECIALLY FOR THE TREATMENT OF CELLULITIS

[76] Inventor: David Holzmann, 25, Boulevard Lannes, 75016 Paris, France

[21] Appl. No.: 871,875

[22] Filed: Jan. 24, 1978

[30] Foreign Application Priority Data

Jan. 24, 1977 [FR] France .................................. 77 01900

[51] Int. Cl.$^2$ ..................... A61K 37/48; A61K 33/16; A61K 31/52
[52] U.S. Cl. ...................................... 424/94; 424/151; 424/253
[58] Field of Search .......................... 424/94, 151, 253

[56] References Cited

U.S. PATENT DOCUMENTS

| | | | |
|---|---|---|---|
| 2,976,212 | 3/1961 | Fredrich et al. | 424/94 |
| 3,978,213 | 8/1976 | Lapinet et al. | 424/180 |

OTHER PUBLICATIONS

Merck Index, 9th ed., 1976, p. 1114 (8368).

Primary Examiner—Leonard Schenkman
Attorney, Agent, or Firm—Sprung, Felfe, Horn, Lynch & Kramer

[57] ABSTRACT

The composition results essentially from the combination of a phosphodiesterase inhibitor and a fluorinated compound. Preferably it comprises theophylline, thiomucase or hyaluronidase, and sodium fluoride, in dosage unit form for topical, injection or ionization local administration.

10 Claims, 2 Drawing Figures

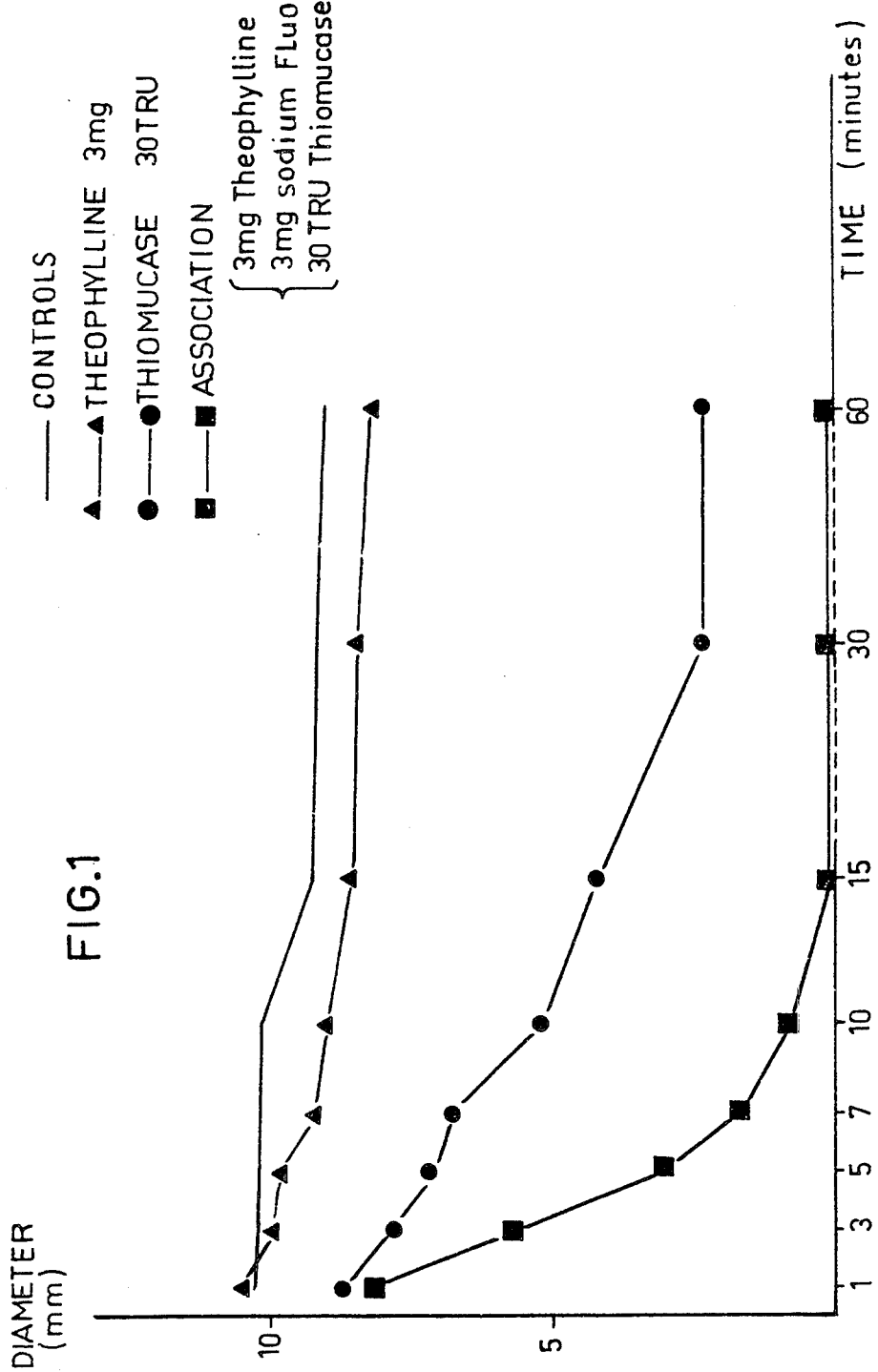

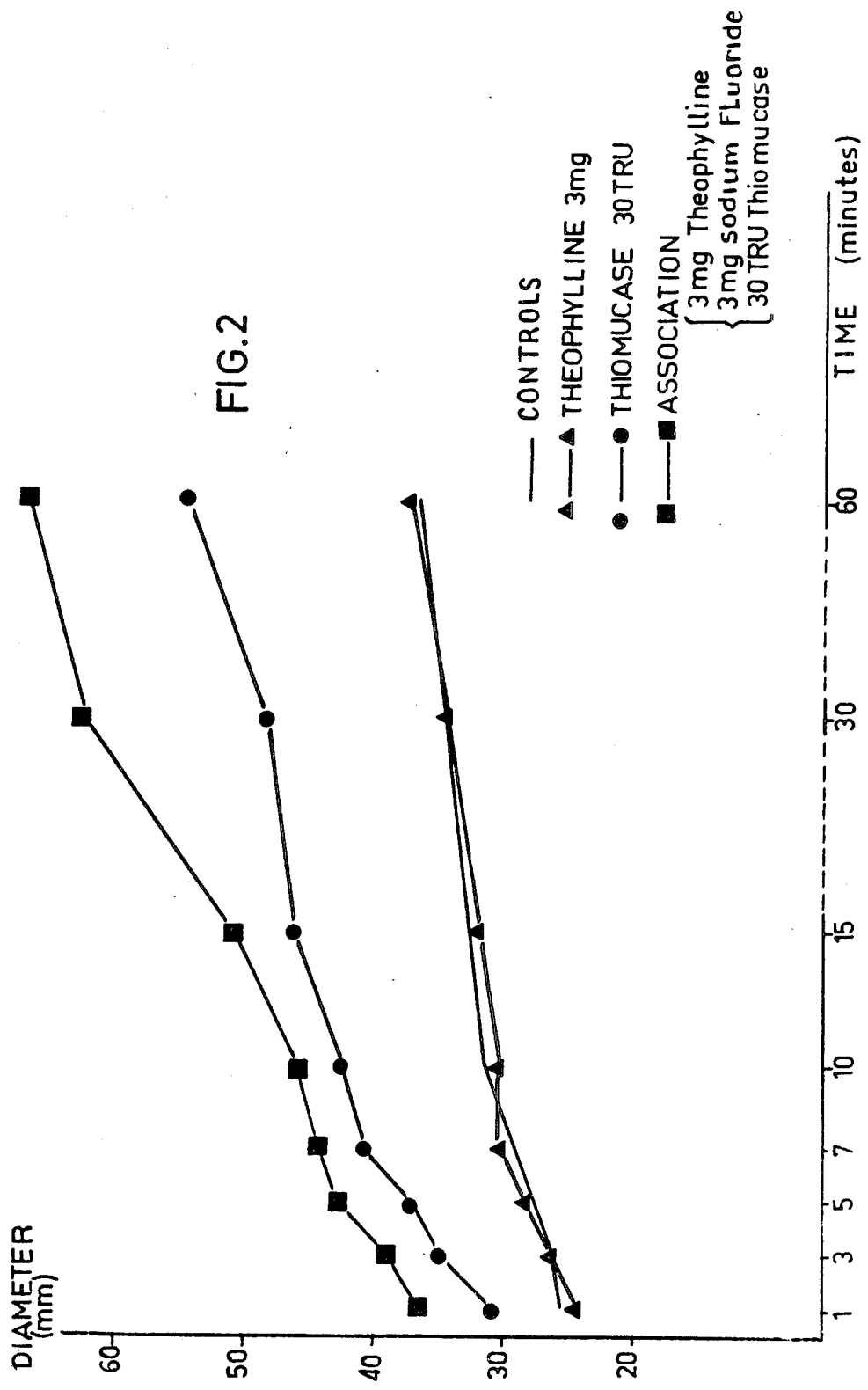

NOVEL MEDICINAL COMPOSITION, ESPECIALLY FOR THE TREATMENT OF CELLULITIS

BACKGROUND OF THE INVENTION

1. Field of the Invention

The present invention relates to a novel composition which can be applied in the medical and esthetic fields. Said composition has particular utility for the treatment of cellulitis.

2. Description of the Prior Art

It has already been suggested to resort to the remarkable properties of the compound named cyclic AMP. It will be recalled that cyclic AMP, also called 3',5' AMPc, or cyclic adenosine 3',5' monophosphoric acid, results from the association of adenine, of ribose and of a phosphoric acid molecule. Cyclic AMP is formed from adenosine triphosphoric acid ATP. This synthesis is carried out by means of an enzymatic system existing in the cellular membrane, that of adenylcyclase, of which the most efficient stimulants are the hormones. Cyclic AMP is present in all the cells.

The degradation of cyclic AMP takes place in the cell under the effect of a phosphodiesterase, which converts it into inactive 5', AMP with the opening of the ring. The phosphodiesterase is inhibited especially by xanthic bases, such as theophylline and caffeine.

The introduction of cyclic AMP into the organism is not free of risk, for this substance can produce undesirable metabolic reactions. In any case, synthetic cyclic AMP does not pass through the cellular membrane. Transcutaneous penetration of cyclic AMP only produces a very slight activity for the substance is rapidly linearized into linear 5', AMP void of activity.

An abundant literature already exists on cyclic AMP and its applications, since the fundamental works of E. W. SUTHERLAND. The following articles may notably be mentioned:

(1) Sutherland E. W. Robison G. A., Butcher R. W.: Some aspects of the biological role of adenosine 3'5' monophosphate (cyclic AMP), circulation, 1968, —37; 279-300.

(2) Robison G. A.; Butcher R. W.; Sutherland E. W.: Cyclic AMP; Am. Rev. Biochem., 1968, 37-149.

(3) Hardman H. G.; Robison G. A.; Sutherland E. W.: Cyclic nucleotides, Am. Rev. Physiol.; 1971; —33; 311.

(4) Hardmann J. G.; O'Malley B. W.; Methods in Enzymology, vol. 38, 1973.

According to the indications of present literature, the treatment of cellulitis by the action of cyclic AMP and an inhibitor of phosphodiesterase by xanthic bases has already given results, but the latter can however be improved.

It is an object of the invention to provide a composition which is useful in the medical and esthetic field.

It is another object of the invention to provide a medicinal composition of improved utility in the treatment of cellulitis.

Other objects and advantages of the present invention will emerge from the description which follows.

GENERAL DESCRIPTION OF THE INVENTION

According to the invention there is provided a composition useful in the medical and esthetic field, in particular for the treatment of cellulitis, said composition resulting essentially from the combination of a phosphodiesterase inhibitor and a fluorinated compound.

By way of phosphodiesterase inhibitor, a known compound is used, or a mixture of such compounds, preferably a xanthic base, such as theophylline and/or caffeine. The known function of such a compound is to prevent the inactivation of the 3',5' AMPc and its conversion into inactive 5' AMP.

By way of fluorinated compound, there is used for example, an inorganic fluoride, such as an alkali or an alkaline earth fluoride or ammonium fluoride, preferably sodium fluoride.

For administration, an association of the inhibitor and of the fluorinated compound is utilized. The essential thing is to produce a suitable cellular concentration of fluorine ions, the latter being situated between 5 and 10 millimoles/liter. The role of the fluorine at the cell level is to strongly stimulate the adenylcyclase, but the mechanism of its action has not been elucidated at the present time. Without limiting the invention to any particular theory, it is thought that in the course of the administration of the new product, the production of AMPc by the adenylcyclase is highly stimulated in avoiding recourse to hormones and to their undesirable secondary effects and in avoiding simultaneously the degradation of AMPc by the phosphodiesterase.

This double effect of adenylcyclase stimulation and phosphodiesterase inhibition enables a potentiating effect to be obtained having as a consequence an optimal intracellular concentration of cyclic AMP, which is situated at 0.5 nanomole/g of fresh cyclic AMP.

According to an improved characteristic of the composition of the invention, the latter may also contain advantageously a depolymerization enzyme, such as thiomucase, α-mucase or hyaluronidase, whose use, conjointly with a phosphodiesterase inhibitor of the xanthic base type, has already been suggested. It is preferred to use thiomucase or hyaluronidase.

It is known that this enzyme has the effect of depolymerizing the long mucopolysaccharide chains of the fundamental substance, responsible for the retention of bound water and of the slowing, by capillary compression, of the diffusion of organic liquids, which eliminate metabolic wastes. Such retention of water and wastes associated with fat overloading of the lipocytes, constitutes classical "pigskin" edema or "orange peel" edema. This depolymerization will therefore cut the long chains of mucopolysaccharides into shorter chains, whence the elimination of the bound water, of wastes, restoration of the venous and lymphatic circulation and disappearance of local edema.

According to the invention, it is possible then to apply the composition in the form of an association with three components (inhibitor, depolymerization enzyme and fluorinated compound) presented in the form of separate or unitary dosage units. A product resulting from the combination of the three aforesaid units has been found to be particularly advantageous for the treatment of cellulitis.

The novel composition may be put into any suitable form for local administration.

It can thus be put into a pharmaceutical form suitable for topical application, such as pomades, creams, gels, ointments and the like. In this case, the composition is intimately mixed in a vehicle capable of enabling the active substance to pass through the cutaneous barrier. Such excipients are known to the man skilled in the art and are already used, for example in medicaments with an anti-inflammatory effect.

Another technique of administration consists of using the composition in a form suitable for injection.

The injections are practiced by the sub-cutaneous or intradermal route in the areas to be treated, so as to enable action in situ. By means of the three components, notably, there is produced at the same time a depolymerization effect on the long mucopolysaccharide chains with the elimination of bound water and increase in cellular and extra-cellular exchanges and a lipolytic action on the triglycerides of the lipocytes. The injections must be repeated until a valid result in the treatment of the cellulitis is produced.

It is also possible to administer the composition according to the invention in a form suitable for ionization.

According to the technique of ionization, an apparatus is used constituted by a galvanic current generator (from 5 to 6 milliamperes), which may or may not be associated with a homofaradic current generator with square pulses (low frequency at 0.2 milliseconds of pulse width and 50 frequencies per second on the average).

The galvanic current enables the transport through the skin, into the sub-cutaneous cellular tissues, of medicament solutions.

If the substance to be ionized is electronegative (thiomucase type enzyme, or anion), the active electrode, bearing the substance to be ionized, is connected to the negative pole of the apparatus.

The dosage units must be provided so as to procure cellular concentrations of fluorine ions on the order of 5 to 10 millimoles/1.

As inhibitor, it is possible to use for example theophylline in the form of injectable ampoules of 4 ml, dosed with 0.24 g of solubilized pure theophylline, in the presence of sodium anisate (6% solution). As an agent with a depolymerizing action, it is possible to put to use lyophilized injectable thiomucase, dosed for example in the proportion of 100 TRU per bottle.

By way of fluorinated compound, there is used, for example, sodium fluoride, presented in the form of an aqueous solution in a suitable dose to produce a cellular concentration of fluorine ions of the order of 5 to 10 millimoles/1.

It is possible to incorporate with the product according to the invention or to use separately on administration various compounds capable of facilitating the treatment or possessing beneficial effects. Thus, is is possible to administer the product at the same time as a small amount of a local anesthetic, such as xylocaine and its derivatives, which are already known in the medication of cellulitis.

In the course of treatment against cellulitis, it may be arranged and even advantageous to associate several administrative forms of the composition. For example, it is possible to carry out a first treatment (attack treatment) by the injection of the composition into the area to be treated by means of a series of intradermal injections. Then a so-called maintenance treatment can take place, in suitable form for the patient, for example a pomade.

For the treatment of cellulitis, the novel composition has a very distinct synergetic effect as is shown by the pharmacological tests reported below. In fact, the overall effect is superior, both in intensity and in duration, by at least 50% with respect to the separate constituents of the composition.

It is also observed that the composition appears to exert an anti-inflammatory action at the level of the treated tissues.

Pharmacological Study

I. In the first series of tests, study of the anticellulitis activity of the following products was undertaken:
(1) theophylline
(2) thiomucase
(3) theophylline+thiomucase+sodium fluoride This study was for the purpose of demonstrating the potentiating action exerted in the composition of the invention (product 3) by the sodium fluoride playing the role of fluorine carrier, relative to the results recorded by using only theophylline and thiomucase in the same standardized test.

Method

The micro-abscess with carragenin in the male rat of about 180 g according to the technique of BENITZ and HALL was used (Arch. Int. Pharmacodyn. 1963, 144, 1 and 2; 185–195).

In this technique, the formation of the abscess was caused by the sub-cutaneous injection, in the carefully shaved dorsal region, of 0.5 ml of a freshly prepared 2 p. 100 solution of carragenin (Marine Colloids Inc. Springfield) in distilled water. The products under study were injected, 24 hours after the constitution of the granuloma, twice daily for two consecutive days, their effect being judged by comparison with animals only receiving, within the same periods, the solvent (9 p. 1000 physiological serum) and studied simultaneously.

Three days after the injection of carragenin, namely 18 hours after the last injection, the animals were sacrificed with ether; the abscesses were removed, carefully dissected and weighted immediately to the nearest milligram. All the abscesses were then placed in an oven at 80° C. for dessication; the latter was continued until constant weights are obtained which were noted.

Conditions of the Study

This study included 40 rats distributed at random into 4 experimental series. The injection of the various substances studied was done in a constant volume equal to 0.3 ml twice daily for two days; the doses were the following: theophylline (10 mg/kg), thiomucase (100 U TRU/kg) and the association thophylline (10 mg/kg+thiomucase (100 U TRU/kg)+fluorine (10 mg/kg) in the form of NaF, namely for example a daily dose for the theophylline equal to 20 mg/kg, this dose being expressed in weight of granuloma. In fact, it was assumed after numerous tests that 24 hours after the creation of the granuloma its weight was on the order of 3 grams, namely an injection by volume of 0.1 ml per 1 gram of fresh granuloma.

RESULTS

The table at the end of the description reports, for each experimental series, the average weight with the standard deviation of the average $$\sqrt{\frac{SX^2 + SX^2/N}{N(N-1)}}$$

of the granulomas in the fresh or dry state and the water content; the percentage of variation and the degree of significance of these variations under the influence of the treatment were investigated by means of the "t" test of Fischer-Student for homogeneous series (one limit) in all cases except for the water content which was investigated by the U test of Mann-Whitney.

COMMENTS 10 mg/kg of theophylline injected 4 times in two days was devoid of anti-cellulitis action; in fact, this compound neither reduced the weight of the granuloma, whether it was fresh or dry, nor the water content.

Thiomucase at 100 U TRU/kg under the same conditions significantly reduced (P=0.0005) by about 35 p. 100 the fresh or dry weight of the granuloma, but no effect on the water content.

The association theophylline+thiomucase+fluorine again reduced very distinctly the weight of the fresh or dry granulomas (of the order of 50 p. 100) whilst on the water content the association had no effect.

The comparison of the fluorinated composition according to the invention with thiomucase confirmed that the association reduces very distinctly the weight of the fresh or dry granuloma; this additional reduction is of the order of 24 p 100 and at the limit of the significance (P=0.05).

CONCLUSION

The association of theophylline, of thiomucase and of fluorine exerts an anti-inflammatory effect on the development of carragenin granuloma. The reduction in the weight of the granuloma is maximum with the association, considerable with thiomucase alone and zero with theophylline. The reduction in weight of the granuloma is indeed due to a reduction of the newly formed inflammatory tissue but not to any reduction in the water content of the granuloma.

II. In another series of tests, a study was undertaken enabling determination of the resorption and diffusion powers of the following products:

(1) theophylline
(2) thiomucase
(3) thiomucase+theophylline+sodium fluoride

The method used was that of Hechter (Anest. Alg. 1959 XVI 3 595) applied in the red rabbit (Fauve de Bourgogne) weighing about 2.2 kg. This method involves study of the influence of the products investigated on the diffusion of a solution of Evans blue.

TECHNIQUE

After careful shaving of two sides of the animal, an intradermal injection was made on the left side of a cubic centimeter of Evans blue at 0.25 p. 100 in solution in isotonic saline serum. In the right side, the animals received under the same conditions an injection of the Evans blue solution, either alone ("control" series) or containing 30 TRU of thiomucase or 3 mg of theophylline or the association composed of 30 TRU of thiomucase, of 3 mg of theophylline and of 3 mg of fluorine (in the form of sodium fluoride). After the injection, the appearance of a rosette centered on an almost black area surrounded by a first blue ring and by a second having a lighter color was noted.

Measurement was made, by means of a caliper square, of the average diameter of the central area and of the light blue outer area: 1-3-5-7-10-15-30 and 60 minutes after the injection. In addition, 24 hours after the injection, the colored resorption of the injection area was estimated by the following notations:

0: skin was perfectly flat at the level of the injection area
1: the skin showed a very slight protuberance
2: marked protuberance
3: bulb of about 5 mm thickness and 15 to 20 mm diameter.

The experiment was carried out on 24 male rabbits, namely 6 rabbits per series.

RESULTS

The results obtained were recorded on two graphs.

FIG. 1 is a graph illustrating the development of the resorption of the pustula. The diameter in millimeters of the areas is recorded in ordinates and the time in minutes is recorded as abscissae;

FIG. 2 is a graph illustrating the development of the diffusion of the Evans blue solution. The diameter in mm of the areas is recorded as ordinates and the time in minutes is recorded as abscissae.

The results obtained, in particular those shown in the graphs, show that there is not, in the controls, a significant difference between the measurements taken on the right side and those on the left side.

Theophylline does not exert up to one hour after the injection on the resorption and diffusion of the Evans blue; on the other hand, 24 hours afterward a distinct reduction in the volume of the pustula was noted since the index is not more than 0.7 instead of 2.8 for the untreated side.

Thiomucase has a distinct action since from the seventh minute there exists a significant difference between the dimensions of the central circle of the treated side and those of the control side. The activity of this product with respect to the diffusion of Evans blue is distinct from the first minute.

Twenty-four hours after the injection, resorption is complete in almost all cases, since the average index is not more than 0.5.

The association composed of theophylline, of thiomucase and of fluorine appears to possess very high visible action from the first minute both as regards resorption and idffusion. When the animals of the thiomucase series are compared with those of the series receiving the association, a superiority of the association is noted since the resorption circle is significantly smaller from the fifth minute and the diffusion circle is greater at 1—10—30 and 60 minutes.

CONCLUSION

Although theophylline only seems to exert an action with regard to resorption, thiomucase and the association theophylline+thiomucase+fluorine are just as active in facilitating resorption and diffusion of Evans blue. However, the association of the three factors is superior to thiomucase alone.

In addition, the results of this second series of tests establish a certain anti-inflammatory effect of the composition according to the invention.

As has been previously indicated, the novel medicament may be utilized in various galenic forms, in particular in the form of a pomade or of injectable ampoules. The excipients for pomades are known rubefacient substances and the most suitable vehicle for injection is a saline solution (physiological solution).

The toxicity of the novel composition is not greater than that of the toxicities of its individual constituents, which are known. Said constituents have in fact already been proposed individually for application in man. It suffices in this respect to refer to the Vidal Dictionary, Edition OVP, Paris, 1976.

The same bibliographical reference shows that the administration in man of all the constituents of the novel composition is devoid of contra-indications. Thus, no contra-indication to the administration of fluorides (sodium, ammonium, calcium), of theophylline and of thiomucase or of hyaluronidase, is known. The composition of the invention is also devoid of contra-indications.

As for the dosage ranges of the novel medicament, it will be adapted to the treated case within the scope for example of an anti-cellulitis treatment. By way of indication, the following amounts may be reported for volumes of 1 ml of injectable solutions:

(1) thiomucase: 100 TRU
  or hyaluronidase: 500 IU;
(2) theophylline: 30 mg;
(3) sodium fluoride: 0.5 mg.

The constituents of the composition may be presented separately, in which case the composition is extemporaneously formed. The composition may also be presented in the form of dosage units prepared in advance, for example, of injectable ampoules of 4 ml. Such ampoules may be administered within the scope of an anti-cellulitis treatment, for example, twice weekly, for several weeks, notably 6 to 8 weeks.

The indications above illustrate the pharmacological properties and the therapeutic application of the novel medicament, which is presented in the form of a novel association of compounds already presented also as medicaments.

The respective proportions of the components of the composition according the invention can vary in wide ranges. These proportions depend especially on the nature of the individual components and on the form of presentation of the composition. Indeed, the man skilled in the art will understand that the proportions of the components vary, for example, according as the composition is presented in the form of an injectable solution or in the form of a cream for local administration.

In the prefered composition, which contains an enzyme, such as thiomucase or hyaluronidase, the enzyme is present in very small quantities, which must be sufficient to permit to have the enzymatic effect. These quantities are usually calculated in active units and not in weight.

Concerning the two others components-phosphodiesterase inhibitor and fluorinated compound—the weight proportions are not veritably critical providing that one pays attention to not pass beyond the allowable limits of toxicity. Generally, the composition may contain, in weight, from 0.1 to 60% of fluorinated compound, the balance being the phosphodiesterase inhibitor, for example theophylline.

I claim:

1. A medicinal composition useful for treating cellulitis, said composition consisting essentially of a xanthic base as a phosphodiesterase inhibitor and a fluorinated compound selected from the group consisting of an alkali metal fluoride, alkaline earth metal fluoride and ammonium fluoride, the inhibitor being present in about 0.1 to 60% by weight of the inhibitor plus fluorinated compound.

2. Medicinal composition according to claim 1, wherein said xanthic base is theophylline or caffeine, alone or in admixture.

TABLE

STUDY OF THE ANTI-CELLULITIS ACTION OF THEOPHYLLINE, OF THIOMUCASE OR OF THE ASSOCIATION THEOPHYLLINE + THIOMUCASE + FLUORINE ON CARRAGENIN GRANULOMA IN THE RAT

| Series | Doses | N | Fresh Granuloma (in g)* $a \pm sd$ | Comparison Against Control | Comparison Against Thiomucase |
|---|---|---|---|---|---|
| "Control" Physiological serum | — | 10 | 4.118 ±0.1875 | | |
| Theophylline | 10 mg/kg | 10 | 3.838 ±0.3015 | −6.8 NS | |
| Thioumucase | 100 U TRU/kg | 10 | 2.718 ±0.2509 | −34.0 0.0005 | |
| Theophylline +Thioumucase +Fluorine | 10 mg/kg | 10 | 2.043 ±0.3326 | −50.4 0.0005 | −24.8 0.05 |

| Series | Doses | N | Dry Granuloma (in g)* $a \pm sd$ | Comparison Against Control | Comparison Against Thiomucase | Water Content (p. 100)** $a \pm sd$ | Comparison Against Control | Comparison Against Thiomucase |
|---|---|---|---|---|---|---|---|---|
| "Control" Physiological Serum | — | 10 | 0.487 ±0.0484 | | | 88.3 ±0.73 | | |
| Theophylline | 10 mg/kg | 10 | 0.416 ±0.0319 | −14.6 NS | | 89.1 ±0.47 | +0.9 NS | |
| Thiomucase | 100 U TRU/kg | 10 | 0.310 ±0.0277 | −36.3 0.005 | | 88.4 ±0.77 | +0.1 NS | |
| Theophylline + Thioumucase + Fluorine | 10 mg/kg | 10 | 0.236 ±0.0392 | −51.5 0.0005 | 23.9 0.05 | 88.6 ±0.20 | +0.3 NS | +0.2 NS |

*According to the t test of Fisher-Student (one limit)
**According to the U test of Man-Whitney (two limits)

3. Composition according to claim 1, in the form of dosage units containing the inhibitor/fluorinated compound association.

4. Composition according to claim 1, containing in addition a depolymerization enzyme selected from the group consisting of thiomucase, α-mucase and hyaluronidase.

5. Composition according to claim 1, in a form suitable for local administration externally and selected from the group consisting of a pomade, ointment, gel and cream.

6. Composition according to claim 1, in the form of dosage units providing concentrations of fluorine ions of the order of 5 to 10 millimoles/liter.

7. Composition according to claim 4, in the form of injectable ampoules containing per ml of solution:
 (1) thiomucase: 100 TRU
   or hyaluronidase: 500 IU;
 (2) theophylline: 30 mg;
 (3) sodium fluoride: 0.5 mg.

8. Method of treating cellulitis in humans or animals, said method comprising administering a composition according to claim 1.

9. Composition according to claim 1, in the form of a solution suitable for injection.

10. Method of treating cellulitis in humans or animals, said method comprising injecting about twice weekly for about 6 to 8 weeks about 4 ml of a solution according to claim 7.

* * * * *